US010010494B2

(12) United States Patent
Zinger

(10) Patent No.: US 10,010,494 B2
(45) Date of Patent: Jul. 3, 2018

(54) METHODS FOR THE TREATMENT OF HYPERHIDROSIS

(76) Inventor: Menni Menashe Zinger, Ashkelon (IL)

(*) Notice: Subject to any disclaimer, the term of this patent is extended or adjusted under 35 U.S.C. 154(b) by 526 days.

(21) Appl. No.: 12/090,439

(22) PCT Filed: Oct. 19, 2006

(86) PCT No.: PCT/IL2006/001205
§ 371 (c)(1),
(2), (4) Date: Apr. 16, 2008

(87) PCT Pub. No.: WO2007/046102
PCT Pub. Date: Apr. 26, 2007

(65) Prior Publication Data
US 2008/0207737 A1 Aug. 28, 2008

Related U.S. Application Data

(60) Provisional application No. 60/727,827, filed on Oct. 19, 2005.

(51) Int. Cl.
A61Q 15/00 (2006.01)
A61K 31/216 (2006.01)
A61K 31/137 (2006.01)
A61K 31/40 (2006.01)
A61K 8/41 (2006.01)
A61K 31/166 (2006.01)
A61K 8/49 (2006.01)

(52) U.S. Cl.
CPC ............... A61K 8/41 (2013.01); A61K 8/415 (2013.01); A61K 8/4913 (2013.01); A61K 31/137 (2013.01); A61K 31/166 (2013.01); A61K 31/216 (2013.01); A61K 31/40 (2013.01); A61Q 15/00 (2013.01)

(58) Field of Classification Search
CPC ...... A43B 17/10; A43B 1/0045; D06M 13/00; D06M 13/005; A61K 9/0014; A61K 15/00; A61K 31/216; A61K 31/137; A61K 31/40; A61K 31/166; A61Q 15/00
See application file for complete search history.

(56) References Cited

U.S. PATENT DOCUMENTS

| 4,747,845 A | 5/1988 | Korol |
| 4,751,236 A | 6/1988 | Mishniot |
| 4,755,386 A | 7/1988 | Hsiao |
| 5,035,068 A | 7/1991 | Biasi |
| 5,112,616 A | 5/1992 | McCarty |
| 5,209,932 A * | 5/1993 | Nichols ............... A61K 8/02 424/409 |
| 5,258,388 A | 11/1993 | Hammer |
| 5,261,169 A | 11/1993 | Williford |
| 5,369,131 A | 11/1994 | Poli |
| 5,411,740 A | 5/1995 | Lee |
| 5,500,222 A | 3/1996 | Lee |
| 5,510,120 A | 4/1996 | Jones |
| 5,580,851 A | 12/1996 | Trinh |
| 5,614,211 A | 3/1997 | Gale |
| 5,730,964 A | 3/1998 | Waldstreicher |
| 5,747,065 A | 5/1998 | Lee |
| 5,790,982 A | 8/1998 | Boutboul |
| 5,843,468 A | 12/1998 | Burkoth |
| 5,908,853 A | 6/1999 | Nahoum |
| 6,004,578 A | 12/1999 | Redwood |
| 6,267,984 B1 | 7/2001 | Beste |
| 6,328,994 B1 | 12/2001 | Shimizu |
| 6,433,003 B1 | 8/2002 | Bobrove |
| 6,517,864 B1 | 2/2003 | Jacobson |
| 6,548,545 B1 | 4/2003 | Thopson |
| 6,562,368 B2 | 5/2003 | Hsu |
| 6,683,049 B1 | 1/2004 | Aoki |
| 6,730,288 B1 | 5/2004 | Abram |
| 6,760,920 B1 | 7/2004 | Kadymir |
| 6,761,903 B2 | 7/2004 | Chen |
| 6,790,435 B1 | 9/2004 | Ma |
| 7,008,637 B2 | 3/2006 | Jacobsen |
| 7,037,571 B2 | 5/2006 | Fish |
| 2002/0018812 A1 | 2/2002 | Busson |
| 2003/0008897 A1 | 1/2003 | Mendel |
| 2003/0211134 A1 | 11/2003 | Wassenaar |
| 2004/0057922 A1 | 3/2004 | Schmid |
| 2004/0072822 A1* | 4/2004 | Leonardi et al. ............. 514/218 |
| 2004/0192754 A1 | 9/2004 | Shapira |
| 2004/0220262 A1* | 11/2004 | Hsu et al. ..................... 514/536 |
| 2005/0064037 A1 | 3/2005 | Chiang |
| 2007/0253911 A1 | 11/2007 | Tamarkin |

FOREIGN PATENT DOCUMENTS

| WO | 2000/054834 A1 | 9/2000 |
| WO | 2004/037225 A2 | 5/2004 |
| WO | 2004/040660 A1 | 5/2004 |
| WO | 2004/041188 A2 | 5/2004 |
| WO | 2005/107812 A1 | 11/2005 |

OTHER PUBLICATIONS

Cheung, Jessie, et al, "Disorders of Sweat Glands: Hyperhidrosis: Unapproved Treatments," Clinics in Dermatology, vol. 20, pp. 638-642 (2002)[hereinafter referred to as "Cheung et al"].*
Hornberger, John, et al, "Recognition, Diagnosis and Treatment of Primary Focal Hyperhidrosis," Journal of the American Academy of Dermatology, vol. 51, Issue 2, pp. 274-286 (Aug. 2004).*
Shaw, Kathy, et al, "Fever as a Sign of Urinary Tract Infection," Clinical Pediatric Emergency Medicine, vol. 1, Issue 2, pp. 117-123 (Mar. 2000).*
Wonderlin, "Muscarinic Blocking Drugs" in "Modern Pharmacology With Clinical Applications," 6th Ed., by Craig et al. (Eds.), Lippincott Williams & Wilkins (Philadelphia, PA), pp. 134-140 (2004).*

(Continued)

Primary Examiner — Theodore R. West

(57) ABSTRACT

The present invention relates in general to methods of treating sweating disorders and in particular to topical compositions for the treatment of hyperhidrosis. The methods of the present invention relate to the topical application of a composition comprising a therapeutically effective amount of oxybutynin, tolterodine or a substituted benzamide such as sulpiride.

21 Claims, No Drawings

(56) References Cited

OTHER PUBLICATIONS

Oishi et al. (Nihon Naibunpi Gakkai Zasshi 59, 1608-19 (1983) (PubMed Abstract 6662241).*
Cheshire et al., "Disorders of Sweating", Semin Neurol., 23(4):399-406 (2003).
Dull, P., "Transdermal oxybutynin for urinary incontinence", American Family Physician (Dec. 15, 2004).
LeWitt, P., "Hyperhidrosis and hypothermia responsive to oxybutynin", Neurology, 38:506-507 (1988).
Wenzel, F. G. et al., "Nonneoplastic disorders of the eccrine glands", J Am Acad Dermatol, 38(1):1-17 (Jan. 1998).
International Search Report for PCT/IL2006/001205 dated Oct. 1, 2007 (2 sheets).
Written Opinion of the International Searching Authority for PCT/IL2006/001205 dated Oct. 1, 2007 (3 sheets).
International Preliminary Report on Patentability for PCT/IL2006/001205 dated Apr. 22, 2008 (4 sheets).

* cited by examiner

METHODS FOR THE TREATMENT OF HYPERHIDROSIS

RELATED APPLICATION DATA

This application is the U.S. national stage of PCT/IL2006/001205 filed on Oct. 19, 2006, which is based on and claims the benefit of U.S. provisional application No. 60/727,827 filed on Oct. 19, 2005, the content of each of which is expressly incorporated herein in its entirety by reference hereto.

FIELD OF THE INVENTION

The present invention relates in general to methods of treating sweating disorders and in particular to topical compositions for the treatment of hyperhidrosis. The methods of the present invention relate to the topical application of a composition comprising a therapeutically effective amount of oxybutynin, tolterodine or a substituted benzamide such as sulpiride.

BACKGROUND

Human secretory glands are primarily divided into 2 types: apocrine and eccrine. Eccrine glands are in higher density on the soles of the feet and the forehead, followed by the palms and the cheeks. Apocrine sweat glands are located primarily in the axilla and urogenital regions. A third type of gland, referred to as apoeccrine glands, develop during puberty and are found primarily in the axillary and perianal areas. The apocrine and apoeccrine glands appear to be responsible for characteristic pheromonal odors, playing no part in temperature regulation.

Eccrine gland sweating is the primary means for body thermoregulation. The eccrine glands are found distributed all over the body in the dermis and epidermis, except for the margins of the limbs, sex organs, and ear drums. The sweat glands are innervated by the sympathetic nervous system and when the body's internal temperature exceeds the hypothalamic set point, activation of a sympathetic reflex causes an increase in sweat output. Evaporation of the sweat leads to a decrease in body temperature.

Hyperhidrosis

Hyperhidrosis, excessive sweating above that required for normal thermoregulation, is a condition that usually begins in childhood or adolescence. People affected with hyperhidrosis sweat more than is needed to cool the body to normal temperature. The disorder is diagnosed when sweating occurs under conditions when normally not expected or is excessive in response to emotional or thermal stimuli. This condition may be idiopathic (also known as primary or essential hyperhidrosis) or secondary to other diseases, metabolic disorders, febrile illnesses, or medication use. Hyperhidrosis affects about 1% of the population and includes people of both sexes and all races (reviewed in Cheshire and Freeman, 2003)

Primary hyperhidrosis is a far more frequent condition than secondary hyperhidrosis and is generally localized to the hands, feet, armpits or a combination of these. Tension and anxiety can elicit or aggravate sweating, but psychological/psychiatric disturbances are only rarely the cause of the disorder.

The primary sites of the body affected with hyperhidrosis, and the associated nomenclature, include:
The palms of the hand, known as palmer hyperhidrosis;
The soles of the feet, known as plantar hyperhidrosis;
The armpits, known as axillary hyperhidrosis;
The head, known as scalp and facial hyperhidrosis;
The trunk or thighs, known as truncal or thigh hyperhidrosis.
The lips, nose, and forehead, known as gustatory hyperhidrosis Many individuals suffer from a combination of the above categories.

Excessive sweating causes embarrassment and discomfort and can lead to emotional distress and occupational disability for the subject. Additionally, hyperhidrosis can aggravate skin disorders like dermatitis and eczema and can result in loss of excess fluids from the body and electrolytes from the body.

Current Treatments for Hyperhidrosis

Current treatments for hyperhidrosis are symptomatic unless a physiological cause is identified. In patients with primary hyperhidrosis or for symptomatic treatment of heavy sweating in patients with secondary hyperhidrosis, not treatable otherwise, treatments include local injections of botulinum toxin, surgical removal of sweat glands, topical deodorants containing aluminum, systemic use of anticholinergic drugs and treatment with electric currents.

Botulinum toxin injections have been shown to have some efficacy in treating hyperhidrosis because of their anticholinergic effects at the neuromuscular junction and in the postganglionic sympathetic cholinergic nerves in the sweat glands. For example BOTOX® is indicated for the treatment of severe primary axillary hyperhidrosis. Agents such as BOTOX® are virtually useless for treating excess sweating in other parts of the body including the palms and back. U.S. Pat. No. 6,683,049 relates to a method of treating a excessive sweating with Botulinum toxin injections.

Sedative and/or anti-cholinergic drugs are effective at reducing sweating but the dosages required to achieve reduced sweating also result in adverse side effects including dryness of the mouth, constipation, blurred vision, decreased sexual ability, lack of appetite, nausea, somnolence, feeling of raised temperature and more. Most patients with localized or generalized hyperhidrosis can not tolerate them for extended periods.

Another treatment option is iontophoresis, which requires the application of a low intensity electric current (15-18 mA) applied to the palms and/or soles immersed in an electrolyte solution. The disadvantages are numerable and include the need for repeated treatments, high cost, recurrence of sweating after cessation, difficulty in applying to axillary region, and impracticality in treating diffuse hyperhidrosis of the face or the trunk/thigh region. The side effects include burning, electric shock, discomfort, tingling and skin irritation. Iontophoresis can be performed in the presence of therapeutic agents, as well. For example, International Patent Application Publication No. WO 00/54834 discloses a sweat control system providing iontophoresis of antiperspirant into a region of the body.

Surgical removal of sweat glands, including thoracoscopic sympathectomy for primary hyperhidrosis is an alternative treatment resulting in some relief to the subject, but can produce undesirable side effects including compensatory sweating.

Hypnosis and laser therapy are other treatment options resulting in some relief to the subject.

Certain pharmaceutical compositions useful for treating hyperhidrosis are known. For example, U.S. Pat. No. 5,730,964 teaches a method of treating sweat related conditions comprising administering orally or topically a therapeutically effective amount of a 5α-reductase inhibitor. U.S. Pat.

No. 6,433,003 teaches a method for the treatment of hyperhidrosis comprising topically administering a composition comprising 0.25% to 6% of a glycopyrrolate compound. U.S. Pat. No. 5,258,388 teaches novel anti-cholinergic/anti-secretory agents useful as mydriatics and as antiperspirants.

US Patent Application Publication No. 20040192754 provides methods for treating idiopathic hyperhidrosis comprising administering to a patient compounds which reduce the activity of a 5-HT2C receptor. The composition comprising the 5-HT2C receptor antagonist can be concurrently administered with antiperspirants, tranquilizers and anti-cholinergic agents.

International Patent Application Publication No. WO 2004/040660 discloses compositions for treating skin wrinkles and hyperhidrosis comprising liminoid constituents, which inhibit acetylcholine release.

Oxybutynin

Oxybutynin (Ditropan®) is an anti-cholinergic agent useful in the treatment of urinary incontinence. Oxybutynin is usually administered in oral form but topical and transdermal compositions for achieving systemic therapeutic levels of the drug for the treatment of urinary incontinence are known in the art.

U.S. Pat. No. 5,900,250 teaches a method for the treatment of neurogenic bladder disorders comprising administering oxybutynin at a therapeutically effective rate to an area of skin; and simultaneously administering a permeation enhancer to the area of skin which is sufficient to substantially increase the permeability of the area to the drug. U.S. Pat. No. 4,747,845 teaches a transdermal synthetic resin matrix system for extended duration drug release and oxybutynin was listed as an agent that could be incorporated into such a system. A transdermal composition and transdermal patch comprising oxybutynin was shown to be effective in treating urinary incontinence (Dull, 2004). Oral oxybutynin was shown to be useful in treating the relatively rare syndrome of episodic hyperhidrosis with hypothermia (LeWitt, 1988).

Various permeation enhancers have been reported for transdermal systemic administration of oxybutynin. For example, U.S. Pat. Nos. 5,411,740; 5,500,222 and 5,614,211, each teach a monoglyceride or a mixture of monoglycerides of fatty acids as a permeation enhancer for an oxybutynin transdermal therapeutic system. U.S. Pat. No. 6,267,984 discloses skin permeation enhancer compositions comprising a monoglyceride and ethyl palmitate for transdermal delivery of oxybutynin. U.S. Pat. No. 5,747,065 discloses a combination of monoglycerides and lactate esters as a permeation enhancing mixture for oxybutynin.

U.S. Pat. No. 5,843,468 describes a dual permeation enhancer mixture of glycerol monolaurate and lauryl acetate for transdermal administration of, inter alia, oxybutynin. U.S. Pat. No. 6,004,578 disclose permeation enhancers selected from the group consisting of alkyl or aryl carboxylic acid esters of polyethyleneglycol monoalkyl ether, and polyethyleneglycol alkyl carboxymethyl ethers for transdermal drug delivery of, inter alia, oxybutynin. U.S. Pat. No. 6,562,368 discloses the use of hydroxide-releasing agent to increase the permeability of skin or mucosal tissue to transdermally administered oxybutynin International Patent Application Publication No. WO 2005/107812 relates to a transdermal composition for enhanced systemic delivery of an anti-cholinergic agent, comprising a urea-containing compound in a carrier system Tolterodine (Detrol®, Detrusitol®) is another anti-cholinergic agent indicated for the treatment of urinary difficulties, including frequent urination and inability to control urination. U.S. Pat. Nos. 6,517,864 and 7,008,637 teach the use of transdermally administered tolterodine as an antimuscarinic agent for the treatment of incontinence.

Sulpiride (Modal®, Dolmatil®, Dogmatyl®, Sulpitil®) is a substituted benzamide neuroleptic agent used to treat stress, dizziness, nausea, vomiting, hypertension, irritable bowel syndrome and ulcer. U.S. Pat. No. 4,751,236 teaches the use of sulpiride for treating genital herpes; U.S. Pat. No. 5,908,853 teaches the use of a combination of an H2 agonist and sulpiride for treating erectile dysfunction.

The above disclosures neither teach nor suggest the topical administration of oxybutynin, tolterodine or a substituted benzamide medication to treat hyperhidrosis.

There remains an unmet need for a treatment for sweating and excess sweating including hyperhidrosis that is noninvasive, excludes undesirable side effects, is easy to administer and is cost effective to the patient.

SUMMARY OF THE INVENTION

The present invention provides for the first time, methods for treating conditions related to overproduction of sweat, including hyperhidrosis, comprising topical application of a dermatological composition comprising a therapeutic agent selected from the group consisting of oxybutynin, tolterodine and a substituted benzamide such as sulpiride. The present invention relates to the unexpected discovery that certain known anti-cholinergic and substituted benzamide therapeutic agents are effective in treating hyperhidrosis when administered topically. Topical application of the therapeutic agents obviates any undesirable systemic effects encountered by oral or transdermal administration.

It was further unexpectedly discovered that oral delivery of tolterodine or sulpiride alleviates hyperhidrosis.

In one aspect the present invention provides a method for treating a sweat related disorder selected from the group consisting of hyperhidrosis, perspiration and apocrine sweating, wherein the method comprises topically administering to a subject in need thereof a dermatological composition comprising a therapeutically effective amount of at least one active agent selected from the group consisting of oxybutynin, tolterodine and a substituted benzamide; and a dermatologically acceptable excipient or carrier.

In various embodiments, the essential ingredient of a topical composition is selected from the group consisting of oxybutynin, tolterodine and a combination of the two. In certain embodiments the dermatological composition comprises oxybutynin. In other embodiments the dermatological composition comprises tolterodine. In other embodiments the substituted benzamide is sulpiride.

In some embodiments the composition is provided in a form selected from the group consisting of an aqueous solution, a non-aqueous solution, a lotion, a cream, a gel, oil, an ointment, foam, mousse, a spray, an emulsion and a microemulsion.

In some embodiments the composition is a gel comprising a therapeutically effective amount of an active agent selected from oxybutynin and tolterodine. In some embodiments oxybutynin is provided in a concentration of about 0.01% to about 5% (weight per volume; w/v). In some preferred embodiments oxybutynin is provided in a concentration of about 0.1% to about 1% (w/v).

In some embodiments tolterodine is provided in a concentration of about 0.002% to about 2% (w/v). In some preferred embodiments, tolterodine is provided in a concentration of about 0.02% to about 0.2% (w/v). In some embodiments the composition comprises a combination of oxybutynin and tolterodine.

In some embodiments the composition comprises as an active agent from about 0.01% to about 5% (w/v) oxybutynin; in a gel formulation. In other embodiments the composition comprises about 0.1% oxybutynin (w/v). A preferred formulation is a gel comprising aloe vera extract.

In various embodiments the composition comprises about 0.002% to about 2% (w/v) in a gel formulation. In yet other embodiments the composition comprises about 0.02% to about 0.2% w/v tolterodine. A preferred formulation is a gel.

In another aspect the present invention provides a method for treating hyperhidrosis comprising administering to a subject in need thereof a composition comprising a therapeutically effective amount of any one of tolterodine or substituted benzamide agent. In preferred embodiment the substituted benzamide agent is sulpiride. In preferred embodiments the composition is administered orally or buccally.

The present invention further provides the use of a compound selected from oxybutynin, tolterodine and a substituted benzamide agent for the preparation of a medicament for the treatment of hyperhidrosis. In some embodiments the compound is selected from oxybutynin, tolterodine and sulpiride for the preparation of a topical medicament. In other embodiments the compound is selected from tolterodine and sulpiride for the preparation of a medicament for the treatment of hyperhidrosis.

In another aspect the present invention provides an article of the class of articles normally juxtaposed to a body, said article comprising a therapeutically effective amount of a therapeutic agent selected from the group consisting of oxybutynin, tolterodine and sulpiride.

In some embodiments the article is selected from the group consisting of a shoe insole, a shoe liner, a sock, a stocking, a glove, a sweatband, an underarm pad, and an undergarment.

These and other embodiments of the present invention will become apparent in conjunction with the description and claims that follow.

DETAILED DESCRIPTION OF THE INVENTION

The present invention provides for the first time an effective and safe pharmaceutical composition for topical administration comprising an anticholinergic agent selected from oxybutynin and tolterodine. The present invention further discloses for the first time the discovery that the substituted benzamide Sulpiride is an effective agent for treating hyperhidrosis.

The present invention provides a method for the treatment of hyperhidrosis and other sweat related disorders comprising topically administering to a subject in need thereof a therapeutically effective amount of an active agent selected from oxybutynin, tolterodine and a substituted benzamide.

It is to be explicitly understood that known pharmaceutical compositions are excluded from the present invention.

Definitions

For convenience and clarity certain terms employed in the specification, examples and claims are described herein.

"Hyperhidrosis" refers to a disease characterized by perspiration in excess of the physiologic amount necessary to maintain thermal homeostasis. Primary or idiopathic hyperhidrosis and secondary hyperhidrosis are the two main categories.

Secondary hyperhidrosis can be caused by a variety of underlying conditions. The association of social anxiety disorder and other psychiatric conditions with hyperhidrosis has also reported. Additionally, secondary hyperhidrosis may be a side effect of certain prescription and non-prescription medications (diaphoretics).

Palmoplantar hyperhidrosis is a common condition in which the eccrine (sweat) glands of the palms (palmer) and soles (plantar) secrete unusually large quantities of sweat. Idiopathic palmoplantar hyperhidrosis begins in childhood and frequently runs in families. Eccrine glands are distributed over most of the body but are most dense in the palms and soles. Patients with hyperhidrosis have normal sweat glands but may have an enhanced response to emotional stimuli (Wenzel and Horn, 1998).

The term "transdermal" drug delivery refers to delivery of a therapeutic agent via the skin surface or mucosal membranes of a subject into the subject's blood stream, thereby providing a systemic effect.

The terms "topical administration" or "topical delivery" refer to the delivery of a therapeutic agent to the skin or mucosa, thereby providing a local, rather than a systemic effect. Topical administration is intended to impart a cutaneous effect, while keeping the pharmacological effects of the drug localized to the intracutaneous regions of contact. Ideally, topical delivery occurs with little or no systemic absorption or accumulation.

A subject refers to a mammal, preferably a human.

As used herein, the phrase "effective amount" and "therapeutically effective amount" describes an amount of the agent that is sufficient to substantially prevent, abrogate or inhibit hyperhidrosis.

Herein, the term "treating" includes abrogating, substantially inhibiting, slowing, substantially ameliorating clinical symptoms or preventing hyperhidrosis. As used herein, the phrase "dermatologically acceptable carrier" refers to a carrier or a diluent that does not cause significant irritation to the skin and does not abrogate the biological activity and properties of the applied therapeutic agent.

Examples of dermatologically acceptable carriers that are useful in the context of the present invention include, without limitation, aqueous and non-aqueous agents. Suitable carriers include aloe vera gel and compositions comprising aloe vera extract or aloe vera gel; alcohols, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose.

In some embodiments a preferred carrier is a gel formulation which contains aloe vera extract or aloe vera gel.

The formulations can further include lubricating agents; wetting agents; antioxidants; emulsifying and suspending agents; and or preservatives.

The compositions of the invention can be formulated so as to provide immediate, sustained or delayed release of the therapeutic agent after administration to the patient by employing formulations known in the art.

Suitable formulations for the therapeutic agents of the present invention include emulsions, creams, aqueous solutions, oils, ointments, pastes, solid sticks, gels, lotions, milks, foams, shampoos, soaps and suspensions.

The judicious choice of ingredients will allow delivery of the active agents whether the active ingredients are water-soluble, poorly water soluble or water insoluble. Combinations of active ingredients that are individually and independently water soluble or insoluble may also be practiced according to the present invention. There are many available solutions to the problem of formulation of poorly soluble ingredients for improved drug bioavailability including the use of surfactants, micelle solutions, emulsions, microemulsions and organic cosolvents, as are well known in the art of dermatological formulations.

In some embodiments the dermatologically acceptable carrier is a hydrophilic carrier. In certain embodiments the composition of the present invention is aqueous based gel or foam. In some embodiments the composition comprises an oil-in-water emulsion, or microemulsion.

In other some embodiments the dermatologically acceptable carrier is a lipophilic carrier. In certain embodiments the composition is a lipid-based ointment or mousse. In some embodiments the composition comprises a water-in-oil emulsion.

The compositions of the present invention can be used concurrently with other methods of treating hyperhidrosis including topical antiperspirants, Botox® injections, iontophoresis and the like.

The dermatologically acceptable carrier of the present invention may include, for example, a thickener, an emollient, an emulsifier, a humectant, a surfactant, a suspending agent, a film forming agent, a foam building agent, a preservative, an antifoaming agent, a fragrance, a lower monoalcoholic polyol, a propellant, a colorant, a pigment or mixtures thereof.

The compositions of the present invention may be manufactured by processes well known in the art, e.g., by means of conventional mixing, dissolving, granulating, dragger-making, levigating, emulsifying, encapsulating, entrapping or lyophilizing processes.

The compositions for use in accordance with the present invention thus may be formulated in conventional manner using one or more physiologically acceptable carriers comprising excipients and auxiliaries, which facilitate processing of the active compounds into preparations which, can be used pharmaceutically.

Oxybutynin

Oxybutynin (Ditropan®, 4-diethylaminobut-2-ynyl2-cyclohexyl-2-hydroxy-2-phenyl-ethanoate) is an antispasmodic, anti-cholinergic agent indicated for the treatment of overactive bladder with symptoms of urge urinary incontinence, urgency, and frequency. Oxybutynin exerts a direct antispasmodic effect on smooth muscle and inhibits the muscarinic action of acetylcholine on smooth muscle. No blocking effects occur at skeletal neuromuscular junctions or autonomic ganglia (antinicotinic effects). Both oral and transdermal compositions comprising oxybutynin are prescribed for treating incontinence. Salts of oxybutynin are encompassed by the present invention, including oxybutynin chloride.

Tolterodine

Tolterodine (Detrol®, Detrusitol®, 2-[3-[bis(1-methylethyl)amino]-1-phenyl-propyl]-4-methyl-phenol) is a competitive muscarinic receptor antagonist. The main effects of tolterodine are an increase in residual urine, reflecting an incomplete emptying of the bladder, and a decrease in detrusor pressure, consistent with an antimuscarinic action on the lower urinary tract.

Following oral administration, tolterodine is metabolized in the liver, resulting in the formation of a 5-hydroxymethyl tolterodine derivative, a major pharmacologically active metabolite. Both tolterodine and the 5-hydroxymethyl metabolite exhibit a high specificity for muscarinic receptors, since both show negligible activity or affinity for other neurotransmitter receptors and other potential cellular targets, such as calcium channels.

Both tolterodine and its active metabolite, 5-hydroxymethyltolterodine, act as competitive antagonists at muscarinic receptors. This results in inhibition of bladder contraction, decrease in detrusor pressure, and an incomplete emptying of the bladder.

Detrol® is tartrate salt of tolterodine.

Sulpiride and Substituted Benzamides

Sulpiride, is the generic name for a substituted benzamide having the chemical name N-[(1-ethylpyrrolidin-2-yl)methyl]-2-methoxy-5-sulfamoyl-benzamide, which is indicated for the treatment of schizophrenia. Sulpiride is a selective dopamine D2 antagonist with antipsychotic and antidepressant activity. Other benzamide derivatives include metoclopramide, tiapride, and sultopride.

Sulpiride, which acts primarily as a dopamine D2 antagonist is more selective than most other neuroleptics which block both dopamine D1 and D2 receptors.

Formulations

The compositions of the invention comprise a dermatologically or cosmetically acceptable carrier to act as a diluent, dispersant or vehicle for the oxybutynin, tolterodine or sulpiride, or combinations thereof so as to facilitate their distribution when the composition is applied to the skin. The compounds may be formulated for application to the hands, feet including soles, face, scalp, neck, trunk, back, limbs, axillae and/or groin of the subject.

Vehicles other than or in addition to water include liquid or solid emollients, solvents, humectants and thickeners. The present invention may be formulated for topical administration in the form of aqueous or non-aqueous solutions, lotions, creams, gels, oils, ointments, foam, mousse, sprays, emulsions, microemulsions, shampoos, soaps and the like.

The dermatological compositions of the present invention preferably exclude penetration enhancers.

In one preferred embodiment, the composition of the invention is a mono-phase composition, i.e. a composition comprising a single solvent system, such as a gel. Non-limiting examples of formulations are as follows:

Gels and Solids

In one embodiment the gel composition comprises aloe vera gel. The Aloe vera (*A. barbadensis*) plant can be separated into two basic products: gel and latex. Aloe vera gel or extract is the leaf pulp or mucilage, a thin clear jelly-like substance obtained from the parenchymal tissue that makes up the inner portion of the leaves. The gel contains carbohydrate polymers, such as glucomannans or pectic acid, plus various other organic and inorganic compounds. Aloe gel has been used for topical treatment of wounds, minor burns, and skin irritations.

A gel comprising an extract of aloe vera was shown to be highly effective as a carrier for oxybutynin and tolterodine. In one preferred embodiment the composition comprises 0.1% w/w oxybutynin and a dermatological carrier comprising aloe vera extract.

Gel compositions can be formulated by simply admixing a suitable thickening agent to the previously described solution or suspension compositions. Examples of suitable thickening agents include, but are not limited to: cross-linked carboxypolymethylene polymers, ethyl cellulose, polyethylene glycols, gum tragacanth, gum karaya, xanthan gums, bentonite and other clays, hydroxyalkyl cellulose, including hydroxyethyl and hydroxypropyl cellulose. The gelled compositions contain an effective concentration of the active agents; from about 5% to about 75% of an organic solvent as previously described; from about 0.5% to about 20% of a thickening agent, and the balance being water, another aqueous carrier or a combination of carriers.

Compositions of solid forms may be formulated as stick-type compositions intended for application to the skin. The solids also contain from about 50% to about 98% of the previously described emollients. This composition can further contain from about 1% to about 20%, of a suitable thickening agent, and, if desired or needed, emulsifiers and water or buffers. Thickening agents previously described with respect to lotions are suitably employed in the compositions in solid form.

Other ingredients, such as preservatives, including methyl-paraben or ethyl-paraben, perfumes, dyes or the like, that are known in the art to provide desirable stability, fragrance or color, or other desirable properties, to compositions for application to the skin.

The compositions formulated as solutions or suspensions may be applied directly to the skin, or, may be formulated as an aerosol and applied to the skin as a spray, foam or mousse. The aerosol compositions further contain from about 20% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as known in the art in a quantity and under a pressure suitable to expel the contents of the container. In the case of a pressurized aerosol, the dosage unit may be determined by providing a valve to deliver a metered amount.

In other embodiments the compositions formulated as solutions, suspensions lotions and gels of the present invention are formulated as a foam or mousse for dermal application.

Foam and Mousse

In certain embodiments foam or mousse formulations are preferred. As used herein, the term "foam" or "mousse" is defined as comprising any lightweight material in cellular form which is made by introducing gas bubbles into liquid.

The pharmaceutical compositions of the present invention, as well as medicaments prepared by using these compositions, may be altered into the form of a foam or mousse by methods known in the art for producing foam or mousse. For detailed description of such methods see for example: US Patent Application Publications 20040057922; 20020018812 and U.S. Pat. Nos. 6,730,288; 5,369,131; International Patent Application Publication No. WO 2004/037225, all incorporated herein by reference. In some embodiments the foamable composition, when placed in an aerosol container and combined with a liquefied gas propellant, releases a therapeutically beneficial foam or mousse product. In other embodiments the composition may be formulated as non-aerosol foam, for example in a propellant free dispenser.

Shampoos and Soaps

The compositions of the present invention may further be formulated as for use as a scalp treatment, shampoo or body wash. Non-limiting examples of compositions for use as a shampoo or soap may be found in U.S. Pat. No. 5,510,120 which discloses a cosmetic composition for topical application to skin and or hair comprising lectin bound particles selected from the group consisting of microcapsules and liposomes.

Ointments

Ointments provide an effective method to apply the active agents to the skin. An ointment can be formulated with a synthetic polymer such as PEG 400 and or PEG 4000 or can be based on mineral oil and petrolatum. In certain embodiments the dermal ointment of the present invention has the following composition: about 0.01% to about 5% (w/w) oxybutynin; about 70% to about 80% (w/w) PEG 400; about 15% to about 25% (w/w) PEG 4000; about 1% to about 15% (w/w) Steareth-20; and about 0.1 to about 1% (w/w) vitamin E.

Other dermal ointment compositions are based on petrolatum and have the following composition: about 0.01% to about 5% (w/w) oxybutynin; about 35% to about 60% (w/w) petrolatum; about 35% to about 55% (w/w) mineral oil; about 1% to about 10% (w/w) Steareth-2; and about 0.1 to about 1% (w/w) vitamin E.

Lotions and Creams

The compositions of the present invention may be provided as a lotion or as a cream and may include at least one or more emollient, which can function as either or both a lubricating and thickening agent. The emollients can comprise in total from about 0.1% to about 50%, preferably from about 1% to about 10%, by weight of the composition. Any emollients known to those of skill in the art as suitable for application to human skin may be used. These include, but are not limited to: hydrocarbon oils and waxes, including mineral oil, petrolatum, paraffin, ceresin, ozokerite, microcrystalline wax, polyethylene, and perhydrosqualene; silicone oils; triglyceride fats and oils, including those derived from vegetable, animal and marine source; including jojoba oil and shea butter; acetoglyceride esters, such as acetylated monoglycerides; ethoxylated glycerides, such as ethoxylated glyceryl monostearate; fatty acids, fatty alcohols and derivatives thereof. Other suitable emollients include lanolin and lanolin derivatives; polyhydric alcohols and polyether derivatives; polyhydric alcohol esters; wax esters; vegetable waxes; phospholipids, such as lecithin and derivatives; sterols, including, but not limited to, cholesterol and cholesterol fatty acid esters; amides, such as fatty acid amides, ethoxylated fatty acid amides, and solid fatty acid alkanolamides.

The lotions may further contain from about 1% to about 10%, more preferably from 2% to 5%, of an emulsifier. The emulsifiers can be nonionic, anionic or cationic. Those with skill in the art may choose emulsifiers suitable for dermal compositions.

Other conventional components of such lotions and creams may be included. One such additive is a thickening agent at a level from 1% to 10% of the composition. Examples of suitable thickening agents were disclosed for the gels, supra.

The lotions and creams are formulated by simply admixing all of the components together. Preferably the oxybutynin, tolterodine and or substituted benzamide is dissolved, suspended or otherwise uniformly dispersed in the mixture.

Solutions and Suspensions

The solutions, which may be aqueous or non-aqueous, are formulated to contain an effective concentration of an active agent.

Suitable organic materials useful as the solvent or a part of a solvent system are as follows: propylene glycol, polyethylene glycol, polypropylene glycol, glycerin, sorbitol esters, 1,2,6-hexanetriol, ethanol, isopropanol, diethyl tartrate, butanediol, and mixtures thereof. Such solvent systems can also contain water.

When the compositions of the invention are formulated as an emulsion, the proportion of the fatty phase may range from about 5% to about 80% by weight, and preferably from about 5% to about 50% by weight, relative to the total weight of the composition. Oils, emulsifiers and co-emulsifiers incorporated in the composition in emulsion form are selected from among those known to those with skill in the cosmetic or dermatological field.

An oil-based topical formulation can be prepared. U.S. Pat. No. 6,761,903 teaches clear oil compositions for improved solubilization of triglycerides and improved delivery of therapeutic agents. The compositions of the '903 patent are preferably formulated for oral delivery but can also be formulated for topical administration.

Articles

The present invention further encompasses certain articles and articles of apparel that come into contact with affected areas of the body and particularly relate to a class of articles normally juxtaposed to a body. The articles can be exposed to, coated with or impregnated with a composition comprising a therapeutic agent selected from oxybutynin, tolterodine and sulpiride. Articles of apparel include garments, footwear, and headgear. Of garments, typically undergarments are those worn usually next to the skin and include underarm perspiration pad, underwear, undershirts, corsetry, including brassieres, girdles, corsets; leotards, tights, pantyhose. Footwear includes hosiery including socks and stockings, shoes, sneakers and insoles and shoe linings. Headgear includes caps, hats and sweatbands.

Suitable articles include for example shoe insoles, shoe liners, socks, stockings, gloves, underarm pads, wrist bands, and the like.

Shoe insoles can be permanent, removable and or disposable. Certain examples of shoe insoles can be found in U.S. Pat. Nos. 5,261,169; 5,035,068 and 7,037,571. Examples of underarm pads can be found in U.S. Pat. Nos. 5,790,982 and 6,760,920.

The articles can be treated with the therapeutic agents, for example, by spraying, imprinting, or by exposure during laundering.

Oral Formulations

For oral administration, the compositions can be formulated by combining tolterodine or the active benzamide compounds with pharmaceutically acceptable carriers known in the art. The compositions can be formulated in any solid or liquid dosage form known in the art, including but not limited to, tablet, caplet, capsule, microcapsule, pellet, pill, powder, syrup, gel, slurry, granule, suspension, dispersion, emulsion, liquid, solution, dragee, bead and beadlet. The oral compositions can be formulated as immediate release formulations, or as controlled or sustained release formulations allowing for extended release of the active ingredient(s) over a predetermined time period. The preferred benzamide derivative is sulpiride.

Suitable excipients for solid formulations include but are not limited to fillers such as sugars, including lactose, sucrose, mannitol, or sorbitol; starch based excipients such as maize starch, wheat starch, rice starch, potato starch and the like, gelatin, gum tragacanth, cellulose based excipients as microcrystalline cellulose, carboxymethylcellulose, hydroxymethylcellulose, hydroxyethylcellulose, methylhydroxypropylcellulose, hydroxypropylcellulose and the like. Polymers such as polyvinylpyrrolidone (PVP) and cross-linked PVP can also be used. In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), surfactants (e.g. sodium lauryl sulfate), and lubricants (e.g. stearic acid, magnesium stearate, polyethylene glycol, sodium lauryl sulfate).

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters. Aqueous carriers include water, alcoholic/aqueous solutions, emulsions, microemulsions or suspensions, including saline and buffered media. Examples of oils include but are not limited to petroleum, animal, vegetable, or synthetic origin, for example, peanut oil, soybean oil, mineral oil, olive oil, sunflower oil, and fish-liver oil. U.S. Pat. No. 6,790,435 teaches stable antiperspirant microemulsions.

Buccal formulations can be prepared using methods known in the art. Non-limiting examples of buccal formulations can be found in U.S. Pat. Nos. 4,755,386; 5,112,616 and 6,328,994.

Dose

The compositions of the present invention are formulated for topical administration of the active ingredients for single or multiple applications. The daily dose of the compounds may vary depending on the medical condition of the patient, the skin status, and the age of the patient. For example, in the treatment of perspiration or apocrine sweating the dose of the therapeutic agent may be less than that needed for treating hyperhidrosis.

Compounds of the present invention may be administered in a single daily dose, or the total daily dose may be administered in divided doses of two, three or four times daily. In some embodiments the formulation is therapeutically effective for a single daily administration. The attending physician can determine the dose. The compound may be applied to the hands, feet, face, scalp, neck, trunk, back, limbs, axillae and/or groin of the human.

Oral sulpiride can be administered at a daily dose of about 10 mg to about 1000 mg; a daily dose of about 100 mg to about 600 mg is preferred.

Additives

The topical composition may additionally include other pharmaceutically acceptable components. The invention also relates to a preferred pharmaceutical preparation according to the invention, which is especially useful for the treatment of hyperhidrosis which are complicated by additional fungal infections, and which further contains an anti-fungal agent. Non-limiting examples of an antifungal include miconazol, clotrimazol, terbinafin, ciclopirox, bifonazol, nystatin, ketoconazol, econazol, and amorolfine. Other additives include colorants, fragrances, stabilizers, preservatives, salts and minerals and the like.

EXAMPLES

Example 1: Compositions Comprising Oxybutynin

Aloe vera composition: Five milliliter (5 ml) commercial gel containing aloe vera extract was mixed with five milligram (5 mg) oxybutynin (0.1% w/v) until a smooth composition formed.

The aloe vera composition comprised Aloe Barbadensis leaf juice, water, and at least one gelling agent. The aloe vera gel may optionally further comprise alcohol, glycerin, one or more emulsifiers such as polysorbate 20, one or more thickening agents such as carbomer, one or more pH balancers such as triethanolamine, one or more preservatives such as methylparaben, and or fragrances and colors.

Topical lotion: 12.5 mg oxybutynin is mixed with 0.25 gram hydroxyethylcellulose and 25 ml purified water to prepare a smooth lotion (0.05% w/v)

Example 2: Compositions Comprising Tolterodine

Aloe vera composition: Five milliliter (5 ml) commercial gel containing aloe vera extract is mixed with one milligram (1 mg) of tolterodine until a smooth composition (0.02% w/v) is formed.

Topical lotion: 2.5 mg tolterodine is mixed with 0.25 gram hydroxyethylcellulose and 25 ml purified water to prepare a smooth lotion (0.01% w/v).

Example 3: Compositions Comprising Sulpiride

A tablet containing 100 mg sulpiride was dissolved in water; added to a gel composition comprising aloe vera extract and mixed to form a smooth composition formed (0.02% w/v).

Example 4: Foam Composition Comprising Oxybutynin or Tolterodine

A non-limiting example of a foam composition is prepared using the ranges of ingredients as follows:

|  | % COMPOSITION (of pressurized liquid) |
| --- | --- |
| Oxybutynin (active principle) | 0.01-5 |
| or Tolterodine (active principle) | 0.002-2 |
| or sulpiride (active principle) | 0.01-5 |
| Xanthan gum (active principle thickener) | 0.2 |
| EDTA bisodium salt (active principle antioxidant) | 0.3 |
| Polysorbate 20 (emulsifier, foaming surfactant) | 4 |
| Polyglycol 300 isostearate (foam thickener) | 4 |
| Purified water | 80.5-86.4 |
| propellant | 5-10 |

EDTA and Xanthan gum are dissolved in the water in a stainless steel dissolving vessel of suitable capacity fitted with a propeller stirrer and turboemulsifier.

Polysorbate, polyglycol and the active agent are added while stirring, and the turboemulsifier is then operated for 15 minutes.

Using a metering pump, the suspension is metered in the volume corresponding to the theoretical weight into aerosol cans while stirring. Each can is immediately sealed by clinching the dispenser valve and is then pressurized by means of the propellant, which is fed in under pressure in a suitable quantity by a pumping device.

Example 5: Administration of the Compositions

The above compositions were tested independently. The subject is a 30 year old male diagnosed with hyperhidrosis. Five ml composition was applied to the back thorax and palms of the subject, who usually sweats profusely. The subject did not sweat from the treated areas for thirty minutes following application. The subject then started to exercise extensively on an exercise bike and did not sweat from the treated areas. The composition was not irritating and the effect lasted several hours.

Example 6: Clinical Trial

Clinical trials to test the efficacy of a composition comprising an anti-cholinergic selected from oxybutynin and tolterodine in treating hyperhidrosis are carried out according to the regulations of the appropriate regulatory authorities. Compositions comprising various concentrations of oxybutynin, tolterodine or sulpiride are tested and compared to carrier alone and to known topical treatments including compositions comprising aluminum salts.

Example 7: Oral Compositions Comprising Sulpiride

Sulpiride is a substituted benzamide indicated for the treatment of: reactive depression, depression associated with psychoses of other origins, for the prophylaxis and treatment of depressive psychoses, schizophrenia, acute delirium, acute hallucinatory and confused states, behavior disorders in all age groups where abnormal aggressive symptoms are in the forefront, duodenal ulceration of psychosomatic origin, vertigo and emesis. Sulpiride has not been indicated for the treatment of hyperhidrosis.

A dose of 200 mg Sulpiride was administered to a patient suffering from hyperhidrosis. The patient immediately noticed a reduction in sweating that began 72 hours after beginning taking the drug and lasted for as long as the patient took a daily pill of 200 mg.

REFERENCES

Cheshire, W P, and Freeman R. Disorders of Sweating. Semin Neurol. 23(4):399-406.2003
Dull, P. Transdermal oxybutynin for urinary incontinence. American Family Physician, Dec. 15, 2004
LeWitt P. Hyperhidrosis and hypothermia responsive to oxybutynin. Neurology. 38:506-507. 1988.
Wenzel F G and Horn T D. Nonneoplastic disorders of the eccrine glands. J Am Acad Dermatol 1998; 38:1-17.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A method for treating a sweat related disorder selected from the group consisting of hyperhidrosis, perspiration and apocrine sweating, wherein the method comprises topically administering to a subject in need thereof a dermatological composition comprising a therapeutically effective amount of at least one active agent selected from the group consisting of oxybutynin, tolterodine and a substituted benzamide; and a dermatologically acceptable excipient or carrier.

2. The method according to claim 1, wherein the active agent is oxybutynin.

3. The method according to claim 2, wherein the oxybutynin is provided in a concentration of about 0.01% to about 5% (w/v).

4. The method according to claim 2, wherein the oxybutynin is provided in a concentration of about 0.1% to about 1% (w/v).

5. The method according to claim 1, wherein the active agent is tolterodine.

6. The method according, to claim 5, wherein the tolterodine is provided in a concentration of about 0.002% to about 2% (w/v).

7. The method according to claim 5, wherein the tolterodine is provided in a concentration of about 0.02% to about 0.2% (w/v).

8. The method according to claim 1, wherein the composition is provided in the form selected from the group consisting of an aqueous solution, a non-aqueous solution, lotion, cream, gel, oil, ointment, foam, mousse, spray, an emulsion, a shampoo, soap and microemulsion.

9. The method according to claim 8, wherein the composition is selected from gel and foam.

10. The method according to claim 9, wherein the gel comprises aloe vera extract or aloe vera gel.

11. The method according to claim 10, wherein the gel composition comprises from about 0.01% to about 5% w/v oxybutynin.

12. The method according to claim 10, wherein the gel composition comprises about 0.1% oxybutynin w/v.

13. The method according to claim 10, wherein the gel composition comprises about 0.002% to about 2% w/v tolterodine.

14. The method according to claim 10, wherein composition comprising about 0.02% to about 0.2% w/v tolterodine.

15. The method according to claim 1, wherein the composition is formulated for application to the hands, feet including soles, face, scalp, neck, trunk, back, limbs, axillae and/or groin of the subject.

16. The method according to claim 1, wherein the composition excludes a permeation enhancer.

17. The method according to claim 1, wherein said therapeutically effective amount of said at least one active agent is comprised by an article selected from the group consisting of a garment, footwear and headgear.

18. The method according to claim 17, wherein the garment is selected from the group consisting of underwear, undershirt, underarm, corsetry, brassiere, girdle, corset, leotards tights and pantyhose.

19. The method according to claim 17, wherein the footwear is selected from the group consisting of a sock, stockings, a shoe, a sneaker, a shoe insole and a shoe lining.

20. The method according to claim 17 therein the headgear is selected from the group consisting of a cap, a hat and a sweatband.

21. A method for treating hyperhidrosis, comprising administering to a subject in need thereof a composition comprising a therapeutically effective amount of tolterodine, wherein the composition is formulated for oral or buccal administration.

* * * * *